United States Patent
Candau

(10) Patent No.: US 6,627,179 B2
(45) Date of Patent: Sep. 30, 2003

(54) SYNERGISTICALLY UV-PHOTOPROTECTING MIXED SUNSCREEN COMPOSITIONS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 10/314,182

(22) Filed: Dec. 9, 2002

(65) Prior Publication Data

US 2003/0157038 A1 Aug. 21, 2003

(30) Foreign Application Priority Data

Dec. 7, 2001 (FR) .......................... 01 15857

(51) Int. Cl.$^7$ .......................... A61K 7/42; A61K 7/144; A61K 7/00
(52) U.S. Cl. .......................... 424/59; 424/60; 424/400; 424/401
(58) Field of Search .......................... 424/59, 60, 400, 424/401

(56) References Cited

FOREIGN PATENT DOCUMENTS

| EP | 0 660 701 B1 | 6/1997 |
| EP | 1 133 980 A2 | 9/2001 |
| WO | WO 97/37634 A1 | 10/1997 |

OTHER PUBLICATIONS

French Search Report Issued for FR 01/15857 on Sep. 27, 2002—2 pages.

*Primary Examiner*—Shelley A. Dodson
(74) *Attorney, Agent, or Firm*—Burns, Doane, Swecker & Mathis, L.L.P.

(57) ABSTRACT

Topically applicable cosmetic/dermatological sunscreen composition well suited for the enhanced UV-photoprotection of human skin and/or hair, contain synergistically UV-A$_{PPD}$-enhancing amounts of (i) at least one UV-screening silicon compound having a benzotriazole functional group substituent, (ii) at least one UV-screening dibenzoylmethane compound, and (iii) at least one UV-screening amino-substituted 2-hydroxybenzophenone compound having the following structural formula (III):

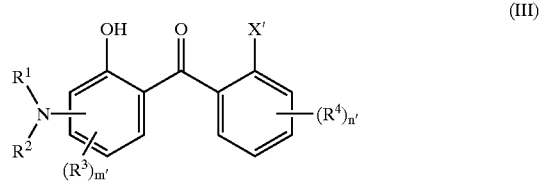

(III)

formulated into (iv) a topically applicable, cosmetically/dermatologically acceptable vehicle, diluent or carrier therefor.

32 Claims, No Drawings

SYNERGISTICALLY UV-PHOTOPROTECTING MIXED SUNSCREEN COMPOSITIONS

CROSS-REFERENCE TO PRIORITY APPLICATION

This application claims priority under 35 U.S.C. §119 of FR-01/15857, filed Dec. 7, 2001, hereby expressly incorporated by reference.

BACKGROUND OF THE INVENTION

1. Technical Field of the Invention

The present invention relates to novel topically applicable cosmetic or dermatological sunscreen compositions well suited for the UV-photoprotection of human skin and/or hair, comprising intimate admixture of (i) at least one UV-screening silicon compound having a benzotriazole functional group substituent, as a first screening agent; (ii) at least one UV-screening dibenzoylmethane compound, as a second screening agent; and (iii) at least one UV-screening specific amino-substituted 2-hydroxybenzophenone compound, as a third screening agent, formulated into (iv) a topically applicable, cosmetically/dermatologically acceptable vehicle, diluent or carrier therefor. The combination of these three UV-screening agents provides synergistic results with regard to the protection factors UV-$A_{PPD}$ conferred.

This invention also relates to a regime or regimen for the UV-protection of the skin and/or hair against the damaging effects of ultraviolet radiation.

2. Description of the Prior Art

It is known to this art that light radiation with wavelengths of from 280 nm to 400 nm permits browning of the human epidermis and that radiation with wavelengths of from 280 to 320 nm, known as UV-B radiation, causes erythemas and skin burns which may be harmful to the development of natural tanning; this UV-B radiation must therefore be screened out from the skin.

It is also known that UV-A radiation, with wavelengths of from 320 to 400 nm, which causes browning of the skin, is capable of causing a detrimental change in the skin, in particular in the case of sensitive skin or of skin continually exposed to solar radiation. UV-A irradiation causes in particular, a loss in the elasticity of the skin and the appearance of wrinkles, resulting in premature aging. UV-A radiation promotes the triggering of the erythemal reaction or accentuates this reaction in certain individuals and can even be the cause of phototoxic or photoallergic reactions. It is therefore also desirable to screen out UV-A radiation.

A wide variety of cosmetic compositions for the photoprotection (UV-A and/or UV-B) of the skin are known to this art.

The efficacy of antisun/sunscreen compositions is generally expressed by the sun protection factor (SPF), which is expressed mathematically by the ratio of the dose of UV radiation necessary to reach the erythemogenic threshold with the UV screening agent to the dose of UV radiation necessary to reach the erythemogenic threshold without UV screening agent. This factor thus relates to the effectiveness of the UV-protection with respect to erythema, the spectrum of biological action of which is centered in the UV-B region, and consequently describes the protection with respect to this UV-B radiation.

In view of the effects of UV-A radiation on the skin and of the availability of numerous compositions comprising combinations of screening agents capable of absorbing UV-B and/or UV-A radiation, specific techniques for evaluating protection against UV-A radiation have been developed.

For the characterization of protection with respect to UV-A radiation, the PPD (Persistent Pigment Darkening) method, which measures the color of the skin observed 2 to 4 hours after exposure of the skin to UV-A radiation, is particularly recommended and used. This method was adopted in 1996 by the Japanese Cosmetic Industry Association (JCIA) as an official test procedure for the UV-A labeling of products and is frequently used by test laboratories in Europe and the United States (Japan Cosmetic Industry Association Technical Bulletin. Measurement Standards for UVA protection efficacy. Issued Nov. 21, 1995 and effective of Jan. 1, 1996).

The sun protection factor UV-$A_{PPD}$ (UV-$A_{PPD}$ PF) is expressed mathematically by the ratio of the dose of UV-A radiation necessary to reach the pigmentation threshold with the UV screening agent ($MPPD_p$) to the dose of UV-A radiation necessary to reach the pigmentation threshold without UV screening agent ($MPPD_{np}$).

$$UV-A_{PPD}PF = \frac{MPPD_p}{MPPD_{np}}$$

These antisun/sunscreen compositions are generally in the form of an emulsion of oil-in-water type (namely, a cosmetically acceptable vehicle composed of a continuous aqueous dispersing phase and of a noncontinuous oily dispersed phase) which comprises, at various concentrations, one or more conventional, lipophilic and/or hydrophilic, organic screening agents capable of selectively absorbing harmful UV radiation, these screening agents (and their amounts) being selected according to the sun protection factors desired.

Cosmetic UV-screening agents constituted from lipophilic silicone compounds substituted with a benzotriazole functional group exhibiting good screening properties, both in the region of UV-A radiation and in the region of UV-B radiation, are known to this art. They are described in EP-A-0,392,883, EP-A-0,660,701, EP-A-0,708,108, EP-A-0,711,778 and EP-A-711,779.

EP-A-0,742,003 and EP-A-0,860,165 describe the combination of these silicone screening agents substituted with a benzotriazole functional group, with specific water-soluble screening agents having a sulfonic functional group, namely, benzene-1,4-di(3-methylidene-10-camphorsulfonic acid) or 2-phenylbenzimidazole-5-sulfonic acid and its salts, for the purpose of producing a synergistic activity with regard to the sun protection factors. These synergistic screening systems require at least one aqueous phase, which dissolves the water-soluble screening agent, and a fatty phase, for dissolving the silicone screening agent, which substantially reduces the formulation possibilities.

Antisun/sunscreen compositions based on amino-substituted 2-hydroxybenzophenone compounds which can contain other additional screening agents, such as silicone derivatives with a benzotriazole functional group or dibenzoylmethane derivatives, are described in EP-A-1,046,391 and DE-10 012 408.

SUMMARY OF THE INVENTION

It has now unexpectedly and surprisingly been determined that a combination or intimate admixture of three specific families of UV-screening compounds, which families are already known per se in this art, namely, immixture of (1) a dibenzoylmethane compound, (2) a benzotriazole silicon compound and (3) a specific amino-substituted 2-hydroxybenzophenone compound, provides synergistic results in terms of exhibiting markedly improved sun protection factors UV-$A_{PPD}$. Such a combination makes it possible to obtain antisun/sunscreen compositions having sun protection factors UV-$A_{PPD}$ which are markedly improved and in any case much higher than those which can be obtained using any of the screening agents alone.

Furthermore, the specific combination of screening agents in accordance with the invention can be easily and readily incorporated in a very wide range of cosmetic vehicles, diluents and carriers.

Thus, the present invention features novel topically applicable cosmetic/dermatological sunscreen compositions, comprising:

(i) at least one UV-screening silicon compound bearing a benzotriazole functional group substituent, as a first screening agent;

(ii) at least one UV-screening dibenzoylmethane derivative, as a second screening agent; and (iii) at least one UV-screening amino-substituted 2-hydroxy-benzophenone compound of formula (III) as defined below, as a third screening agent, formulated into (iv) a topically applicable, cosmetically/dermatologically acceptable vehicle, diluent or carrier therefor.

The present invention also features a regime or regimen for the photoprotection of the skin and/or hair against the deleterious effects of ultraviolet radiation, in particular solar radiation.

Generally, the said first, second and third UV-screening agents are present in the compositions of the invention in a proportion producing a synergistic effect with regard to the sun protection factors UV-$A_{PPD}$ conferred.

DETAILED DESCRIPTION OF BEST MODE AND SPECIFIC/PREFERRED EMBODIMENTS OF THE INVENTION

More particularly, the silicon compounds bearing a benzotriazole functional group substituent according to the present invention are preferably silanes or siloxanes with a benzotriazole functional group comprising at least one structural unit of the following formula (1):

$O_{(3-a)/2}Si(R_7)_a$-G    (1)

in which $R_7$ is an optionally halogenated $C_1$–$C_{10}$ alkyl radical, or a phenyl radical, or a trimethylsilyloxy radical, a is an integer ranging from 0 to 3, inclusive; and G is a monovalent radical bonded directly to a silicon atom which corresponds to the following structural formula (2):

(2)

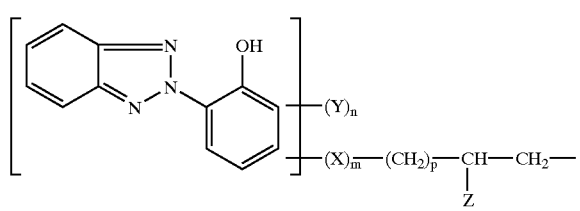

in which the radicals Y, which may be identical or different, are each a $C_1$–$C_8$ alkyl radical, a halogen, or a $C_1$–$C_4$ alkoxy radical, with the proviso that, in the latter event, two adjacent Y radicals on the same aromatic nucleus can together form an alkylidenedioxy group in which the alkylidene group has from 1 to 2 carbon atoms; X is O or NH; Z is hydrogen or a $C_1$–$C_4$ alkyl radical; n is an integer ranging from 0 to 3, inclusive; m is 0 or 1, and p is an integer ranging from 1 to 10, inclusive.

These compounds are described, in particular, in EP-A-0,392,883, EP-A-0,660,701, EP-A-0,708,108, EP-A-0,711,778 and EP-A-711,779.

The silicon compounds according to the present invention preferably belong to the general family of the benzotriazole silicones which is described, in particular, in EP-A-0,660,701.

One family of benzotriazole silicones which is particularly well suited for the implementation of the present invention is that comprising the compounds corresponding to the following formulae (5) or (6):

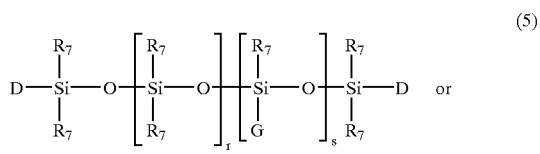

(5)

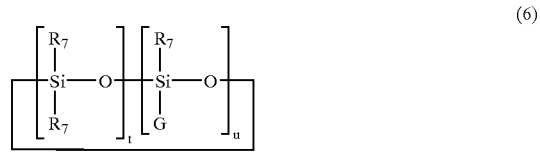

(6)

in which the radicals $R_7$, which may be identical or different, are each a $C_1$–$C_{10}$ alkyl, phenyl, 3,3,3-trifluoropropyl or trimethylsilyloxy radical, at least 80% by number of the $R_7$ radicals being methyl; the radicals D, which may be identical or different, are each a $R_7$ radical or the G radical; r is an integer ranging from 0 to 50, inclusive, and s is an integer ranging from 0 to 20 inclusive, and, if s=0, at least one of the two D symbols denotes G; u is an integer ranging from 1 to 6, inclusive, and t is an integer ranging from 0 to 10, inclusive, with the proviso that t+u is equal to or greater than 3; and the G symbol corresponds to the above formula (2).

As will be seen from the formula (2) given above, the bonding of the —(X)$_m$—(CH$_2$)$_p$—CH(Z)—CH$_2$— radical to the benzotriazole structural unit, which therefore ensures that the benzotriazole unit is bonded to the silicon atom of the silicone chain, can be at any available position presented by the two aromatic nuclei of the benzotriazole:

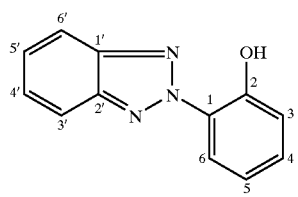

Preferably, this attachment is at the 3-, 4- or 5-position (aromatic nucleus bearing the hydroxyl functional group) or 4'-position (benzene nucleus adjacent to the triazole ring) and even more preferably at the 3-, 4- or 5-position. In a preferred embodiment of the invention, the attachment is at the 3 position.

Likewise, the attachment of the Y substituent unit or units can be at any other position available within the benzotriazole. However, this attachment preferably is at the 3-, 4-, 4'-, 5- and/or 6-position. In a preferred embodiment of the invention, the attachment of the Y unit is at the 5 position. In the above formulae (5) and (6), the alkyl radicals can be linear or branched and are selected, in particular, from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred $R_7$ alkyl radicals according to the invention are the methyl, ethyl, propyl, n-butyl, n-octyl and 2-ethylhexyl radicals. Even more preferably, the $R_7$ radicals are all methyl radicals. Among the compounds of formulae (5) or (6) above, it is preferable to employ those corresponding to the formula (5), namely, diorganosiloxanes with a short linear chain. Among the compounds of formula (5) above, it is preferable to employ those in which the D radicals are both $R_7$ radicals. More particularly preferred linear diorganosiloxanes within the scope of the present invention are statistical derivatives or, alternatively, block-defined derivatives exhibiting at least one and more preferably all of the following characteristics:

D is an $R_7$ radical;

$R_7$ is alkyl and more preferably is methyl;

r ranges from 0 to 15, inclusive; s ranges from 1 to 10, inclusive;

n is not zero and preferably is equal to 1 and Y is then methyl, tert-butyl or $C_1$–$C_4$ alkoxy;

Z is hydrogen or methyl;

m=0 or [m=1 and X=O]; and p is equal to 1.

One family of benzotriazole silicones which is particularly well suited according to this invention is that having the following structural formula (7):

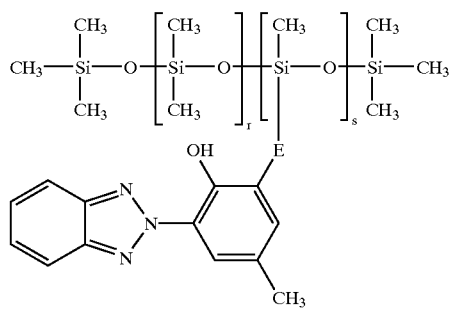

with $0 \leq r \leq 10$, $1 \leq s \leq 10$, and where E represents the divalent radical:

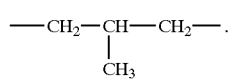

In a particularly preferred embodiment of the invention, the benzotriazole silicone is the compound Drometrizole Trisiloxane (CTFA name) having the following structural formula:

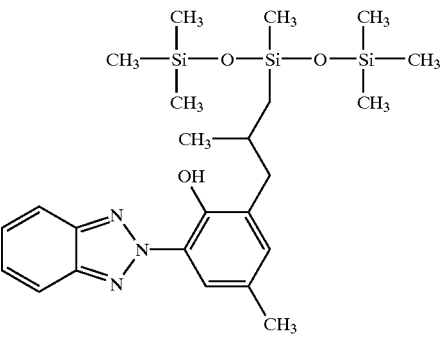

Processes suitable for the preparation of the compounds of formulae (1), (5), (6) and (7) above are described, in particular, in U.S. Pat. Nos. 3,220,972, 3,697,473, 4,340, 709, 4,316,033, and 4,328,346 and in EP-A-0,392,883 and EP-A-0,742,003.

The silicon compound with a benzotriazole functional group is advantageously present in the compositions according to the invention at contents ranging from 0.5% to 20%, preferably ranging from 1% to 10%, by weight, and more preferably from 2% to 8% by weight, with respect to the total weight of the composition.

As indicated above, the dibenzoylmethane compounds according to the present invention are compounds which are already well-known per se and which are described, in particular, in FR-A-2,326,405, FR-A-2,440,933 and EP-A-0,114,607, hereby expressly incorporated by reference, as is each other patent/application referred to herein.

Particularly exemplary dibenzoylmethane compounds according to the present invention include:

2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

Very particularly preferred is 4-tert-butyl-4'-methoxydibenzoylmethane, in particular that marketed under the trademark "Parsol 1789" by Hoffmann-LaRoche, this UV-screening agent having the following expanded formula (I):

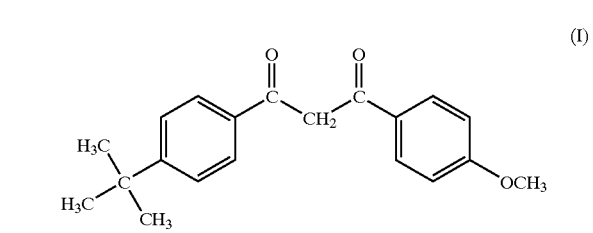

Another preferred dibenzoylmethane derivative according to the present invention is 4-isopropyldibenzoylmethane, a UV-screening agent marketed under the trademark "Eusolex 8020" by Merck and having the following expanded formula (II):

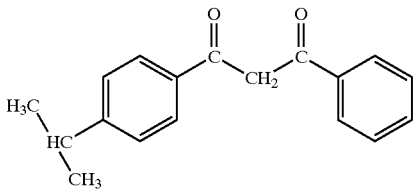

(II)

The dibenzoylmethane derivative or derivatives are advantageously present in the compositions of the invention at contents preferably ranging from 0.5% to 20% by weight and more preferably from 1% to 10% by weight and even more preferably from 2% to 8% by weight, with respect to the total weight of the composition.

The amino-substituted 2-hydroxybenzophenone compounds in accordance with the invention have the following formula (III):

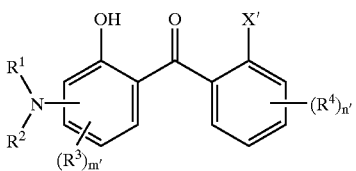

(III)

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$alkoxycarbonyl radical, a $C_1$–$C_{12}$ alkylamino radical, a di$(C_1$–$C_{12})$alkylamino radical, an aryl radical or a heteroaryl radical which is optionally substituted, or a water-solubilizing substituent selected from among a carboxylate group, a sulfonate group or an ammonium residue; X' is a hydrogen atom or a —COOR$^5$ or —CONR$^6$R$^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(Y'O)$_o$—Z' radical or an aryl radical; Y' is —(CH$_2$)$_2$—, —(CH$_2$)$_3$—, —(CH$_2$)$_4$— or —CH—(CH$_3$)—CH$_2$—; Z' is —CH$_2$—CH$_3$, —CH$_2$CH$_2$CH$_3$, —CH$_2$—CH$_2$—CH$_2$—CH$_3$ or —CH(CH$_3$)—CH$_3$; m' is an integer ranging from 0 to 3; n' is an integer ranging from 0 to 3; and o is an integer ranging from 1 to 2.

Representative $C_1$–$C_{20}$ alkyl radicals include, for example: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Representative $C_2$–$C_{10}$ alkenyl radicals include, for example: vinyl, n-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Representative $C_1$–$C_{12}$ alkoxy radicals include, for example: methoxy, ethoxy, n-propoxy, n-butoxy, n-pentoxy, 1-methylpropoxy, 3-methylbutoxy, 2,2-dimethylpropoxy, 1-methyl-1-ethylpropoxy, octoxy, 2-methylpropoxy, 1,1-dimethylpropoxy, hexoxy, heptoxy or 2-ethylhexoxy.

Representative $C_3$–$C_{10}$ cycloalkyl radicals include, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Representative $C_3$–$C_{10}$ cycloalkenyl radicals having one or more double bonds include, for example: cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can be substituted by one or more substituents (preferably from 1 to 3) selected, for example, from among halogen, such as chlorine, fluorine or bromine; cyano; nitro; amino; $C_1$–$C_4$ alkylamino; di$(C_1$–$C_4)$alkylamino; $C_1$–$C_4$ alkyl; $C_1$–$C_4$ alkoxy; or hydroxyl. They can also contain from 1 to 3 heteroatoms, such as sulfur, oxygen or nitrogen, the free valencies of which can be satisfied by a hydrogen atom or a $C_1$–$C_4$ alkyl radical.

The aryl radicals are preferably phenyl or naphthyl which can comprise one or more substituents (preferably from 1 to 3) selected, for example, from among halogens, such as chlorine, fluorine or bromine; cyano; nitro; amino; $C_1$–$C_4$ alkylamino; di$(C_1$–$C_4)$alkylamino; $C_1$–$C_4$ alkyl; $C_1$–$C_4$ alkoxy; or hydroxyl. Particularly preferred are phenyl, methoxyphenyl and naphthyl.

The heteroaryl radicals generally comprise one or more heteroatoms selected from among sulfur, oxygen or nitrogen.

The water-solubilizing groups are, for example, carboxylate or sulfonate groups and more particularly their salts with physiologically acceptable cations, such as alkali metal salts or trialkylammonium salts, such as tri(hydroxyalkyl)-ammonium or 2-methylpropan-1-ol-2-ammonium salts. Also exemplary are ammonium groups, such as alkylammoniums, and their salified forms with physiologically acceptable anions.

Particularly exemplary of the 5- or 6-membered heterocyclic ring members formed by the $R^1$ and $R^2$ radicals with the nitrogen atom are pyrrolidine or piperidine.

The amino groups can be bonded to the benzene ring in the ortho, meta or para position with respect to the carbonyl radical and more preferably in the para position.

One family of preferred compounds of formula (III) comprises those having the following structural formula (IIIa):

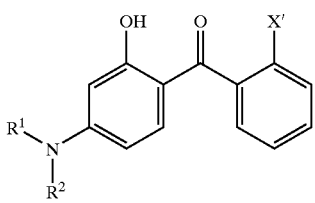

(IIIa)

in which $R^1$ and $R^2$, which may be identical or different, are each a hydrogen atom or a $C_1$–$C_{12}$ alkyl radical, or together form, with the nitrogen atom to which they are bonded, a 5- or 6-membered heterocyclic ring member; X' is —COOR$^5$ or —CONR$^6$ R$^7$; $R^5$ is a hydrogen atom, a $C_1$–$C_{12}$ alkyl radical or a $C_3$–$C_6$ cycloalkyl radical; and $R^6$ and $R^7$, which may be identical or different, are each a hydrogen atom, a $C_1$–$C_{12}$ alkyl radical or a $C_5$–$C_6$ cycloalkyl radical.

The more particularly preferred compounds of formula (IIIa) are those in which $R^1$ and $R^2$, which may be identical or different, are each a $C_1$–$C_4$ alkyl radical and more particularly ethyl; $R^5$ is a $C_3$–$C_8$ alkyl radical; and $R^6$ and $R^7$, which may be identical or different, are each a $C_1$–$C_8$ alkyl radical.

Another family of preferred compounds of formula (III) comprises those having the following structural formula (IIIb):

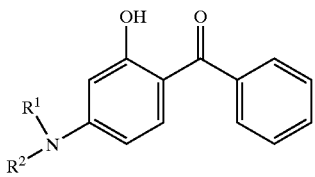

(IIIb)

in which $R^1$ and $R^2$, which may be identical or different, are each a $C_1$–$C$ 2 alkyl radical, or together form, with the nitrogen atom to which they are bonded, a 5-or 6-membered heterocyclic ring member.

Particularly exemplary of the compounds of formula (IIIb) are:

4-diethylamino-2-hydroxyphenyl phenyl ketone,
4-pyrrolidino-2-hydroxyphenyl phenyl ketone.

A family of more particularly preferred compounds of formula (III) comprises those having the following structural formula (IIIc):

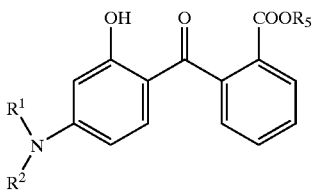

(IIIc)

in which $R^1$ and $R^2$, which may be identical or different, are each a hydrogen atom or a $C_1$–$C_8$ alkyl radical, or together form, with the nitrogen atom to which they are bonded, a 5- or 6-membered heterocyclic ring member; and $R^5$ is a hydrogen atom, a $C_1$–$C_{12}$ alkyl radical or a $C_3$–$C_6$ cycloalkyl radical.

Exemplary compounds of formula (IIIc) are:
2-(4-pyrrolidino-2-hydroxybenzoyl)benzoic acid,
methyl 2-(4-diethylamino-2-hydroxybenzoyl)benzoate,
2-ethylhexyl 2-(4-diethylamino-2-hydroxybenzoyl)-benzoate,
cyclohexyl 2-(4-diethylamino-2-hydroxybenzoyl)-benzoate,
n-hexyl 2-(4-diethylamino-2-hydroxybenzoyl)benzoate,
2-(4-dibutylamino-2-hydroxybenzoyl)benzoic acid,
methyl 2-(4-dibutylamino-2-hydroxybenzoyl)benzoate, and
isobutyl 2-(4-dibutylamino-2-hydroxybenzoyl)benzoate.

A very particularly preferred compound of formula (III) is n-hexyl 2-(4-diethylamino-2-hydroxy-benzoyl) benzoate.

The compounds of formula (I) as defined above are known per se and their structures and syntheses thereof are described in EP-1,046,391 and DE-100 12 408, also expressly incorporated by reference.

The amino-substituted 2-hydroxybenzophenone compound according to this invention are preferably present in the compositions of the invention in proportions ranging from 0.1% to 20% by weight, preferably from 0.1% to 15% by weight, and more preferably from 0.5% to 10% by weight with respect to the total weight of the composition.

The compositions according to this invention can additionally comprise at least one organic photoprotective agent and/or at least one inorganic photoprotective agent which are active in the UV-A and/or UV-B regions (absorbers), such photoprotective agents being water-soluble, fat-soluble or insoluble in commonly used cosmetic solvents.

The organic UV-photoprotective agents are selected, in particular, from among the anthranilates; cinnamic derivatives; dibenzoylmethane derivatives; salicylic derivatives; camphor derivatives; triazine derivatives, such as those described in U.S. Pat. Nos. 4,367,390 and 4,724,137, EP-863,145, EP-517,104, EP-570,838, EP-796,851, EP-775,698, EP-878,469, EP-933,376, EP-507,691, EP-507,692, EP-790,243 and EP-944,624; benzophenone derivatives, other than those of formula (III); β,β-diphenylacrylate derivatives; benzotriazole derivatives; benzalmalonate derivatives; benzimidazole derivatives; imidazolines; bisbenzoazolyl derivatives as described in EP-669, 323 and U.S. Pat. No. 2,463,264; p-aminobenzoic acid (PABA) derivatives; methylenebis (hydroxyphenylbenzotriazole) derivatives as described in U.S. Pat. Nos. 5,237,071 and 5,166,355, GB-2,303,546, DE-197 26 184 and EP-893,119; screening polymers and screening silicones, such as those described, in particular, in WO-93/04665; dimers derived from α-alkylstyrene, such as those described in DE-198 55 649; 4,4-diarylbutadienes as described in EP-0,967,200, DE-197 55 649 and EP-1,333, 981 and mixtures thereof.

Exemplary organic photoprotective agents which are active in the UV-A and/or UV-B regions are indicated below under their INCI names:

para-Aminobenzoic Acid Derivatives:
PABA,
Ethyl PABA,
Ethyl Dihydroxypropyl PABA,
Ethylhexyl Dimethyl PABA, marketed, in particular, under the trademark "Escalol 507" by ISP,
Glyceryl PABA,
PEG-25 PABA, marketed under the trademark "Uvinul P25" by BASF, Salicylic Derivatives:
  Homosalate, marketed under the trademark "Eusolex HMS" by Rona/EM Industries,
  Ethylhexyl Salicylate, marketed under the trademark "Neo Heliopan OS" by Haarmann and Reimer,
  Dipropyleneglycol Salicylate, marketed under the trademark "Dipsal" by Scher,
  TEA Salicylate, marketed under the trademark "Neo Heliopan TS" by Haarmann and Reimer,
Cinnamic Derivatives:
  Ethylhexyl Methoxycinnamate, marketed, in particular, under the trademark "Parsol MCX" by Hoffmann-LaRoche,
  Isopropyl Methoxy cinnamate,
  Isoamyl Methoxy cinnamate, marketed under the trademark "Neo Heliopan E 1000" by Haarmann and Reimer,
  Cinoxate,
  DEA Methoxycinnamate,
  Diisopropyl Methylcinnamate,
  Glyceryl Ethylhexanoate Dimethoxycinnamate,
β,β-Diphenylacrylate Derivatives:
  Octocrylene, marketed, in particular, under the trademark "Uvinul N539" by BASF,
  Etocrylene, sold marketed, in particular, under the trademark "Uvinul N35" by BASF,
Benzophenone Derivatives:
  Benzophenone-1, marketed under the trademark "Uvinul 400" by BASF,
  Benzophenone-2, marketed under the trademark "Uvinul D50" by BASF,
  Benzophenone-3 or Oxybenzone, marketed under the trademark "Uvinul M40" by BASF,
  Benzophenone-4, marketed under the trademark "Uvinul MS40" by BASF,
  Benzophenone-5,
  Benzophenone-6, marketed under the trademark "Helisorb 11" by Norquay,
  Benzophenone-8, marketed under the trademark "Spectra-Sorb UV-24" by American Cyanamid,
  Benzophenone-9, marketed under the trademark "Uvinul DS-49" by BASF,
  Benzophenone-12,
Benzylidenecamphor Derivatives:
  3-Benzylidene camphor, marketed under the trademark "Mexoryl SD" by Chimex,
  Benzylidene Camphor Sulfonic Acid, marketed under the trademark "Mexoryl SL" by Chimex,
  Camphor Benzalkonium Methosulfate, marketed under the trademark "Mexoryl SO" by Chimex,
  Terephthalylidene Dicamphor Sulfonic Acid, marketed under the trademark "Mexoryl SX" by Chimex,
  Polyacrylamidomethyl Benzylidene Camphor, marketed under the trademark "Mexoryl SW" by Chimex,
Phenylbenzimidazole Derivatives:
  Phenylbenzimidazole Sulfonic Acid, marketed, in particular, under the trademark "Eusolex 232" by Merck,
  Disodium Phenyl Dibenzimidazole Tetrasulfonate marketed under the trademark "Neo Heliopan AP" by Haarmann and Reimer,
Triazine Derivatives:
  Anisotriazine, marketed under the trademark "Tinosorb S" by Ciba Specialty Chemicals,
  Ethylhexyl triazone, marketed, in particular, under the trademark "Uvinul T150" by BASF,
  Diethylhexyl Butamido Triazone, marketed under the trademark "Uvasorb HEB" by Sigma 3V,
  2,4,6-tris(diisobutyl 4'-aminobenzalmalonate)-s-triazine,
Phenylbenzotriazole Derivatives:
  Drometrizole Trisiloxane, marketed under the trademark "Silatrizole" by Rhodia Chimie,
  Methylenebis(benzotriazolyltetramethylbutylphenol), marketed in the solid form under the trademark "Mixxim BB/100" by Fairmount Chemical or in the micronized form in aqueous dispersion under the trademark "Tinosorb M" by Ciba Specialty Chemicals,
Anthranilic Derivatives:
  Menthyl anthranilate, marketed under the trademark "Neo Heliopan MA" by Haarmann and Reimer,
Imidazoline Derivatives:
  Ethylhexyl Dimethoxybenzylidene Dioxoimidazoline Propionate,
Benzalmalonate Derivatives:
  Polyorganosiloxane comprising benzalmalonate functional group, marketed under the trademark "Parsol SLX" by Hoffmann-LaRoche, and mixtures thereof.
4,4-Diarylbutadiene Derivatives:
  1,1-Dicarboxy(2,2'-dimethylpropyl)-4,4-dipenylbutadiene, and mixtures thereof.

The organic UV-photoprotective agents which are more particularly preferred are selected from among the following compounds:
  Ethylhexyl Salicylate,
  Butyl Methoxydibenzoylmethane,
  Ethylhexyl Methoxycinnamate,
  Octocrylene,
  Phenylbenzimidazole Sulfonic Acid,
  Benzophenone-3,
  Benzophenone-4,
  Benzophenone-5,
  4-Methylbenzylidene Camphor,
  Disodium Phenyl Dibenzimidazole Tetrasulfonate,
  Anisotriazine,
  Ethylhexyl triazone,
  Diethylhexyl Butamido Triazone,
  Methylenebis(benzotriazolyltetramethylbutylphenol),
  Drometrizole Trisiloxane,
  2,4,6-Tris(diisobutyl 4'-aminobenzalmalonate)-s-triazine,
and mixtures thereof.

The inorganic UV-photoprotective agents are typically selected from among pigments or alternatively nanopigments (mean size of the primary particles: generally ranging from 5 nm to 100 nm, preferably from 10 nm to 50 nm) formed from coated or uncoated metal oxides, such as, for example, nanopigments formed from titanium dioxide (amorphous or crystallized in the rutile and/or anatase form), iron oxide, zinc oxide, zirconium oxide or cerium oxide, and mixtures thereof. Conventional coating agents are, furthermore, alumina and/or aluminum stearate. Such coated or uncoated metal oxide nanopigments are described, in particular, in EP-518,772 and EP-518,773.

The compositions according to the invention can also comprise agents for the artificial tanning and/or browning of the skin (self-tanning or artificial/sunless tanning agents), such as, for example, dihydroxyacetone (DHA).

The compositions in accordance with the present invention can additionally comprise conventional cosmetic additives and adjuvants selected, in particular, from among fatty substances, organic solvents, ionic or nonionic thickeners, softeners, antioxidants, agents for combating free radicals, opacifiers, stabilizers, emollients, silicones, a-hydroxy acids, antifoaming agents, moisturizing agents, vitamins, insect repellents, substance P antagonists, anti-inflammatories, fragrances, preservatives, surfactants, fillers, polymers, propellants, basifying or acidifying agents, colorants or any other ingredient commonly used in the cosmetic and/or dermatological field, in particular for the production of self-tanning compositions in the form of emulsions.

The fatty substances can be an oil or a wax, or mixture thereof. By the term "oil" is intended a compound which is liquid at ambient temperature. By the term "wax" is intended a compound which is solid or substantially solid at ambient temperature and for which the melting point is generally greater than 35° C.

Exemplary oils are mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate marketed under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; polyalkylenes and their mixtures.

Exemplary waxy compounds are paraffin wax, carnauba wax, beeswax or hydrogenated castor oil.

And exemplary organic solvents include the lower alcohols and polyols having at most 8 carbon atoms.

The thickeners are advantageously selected, in particular, from among the crosslinked polyacrylic acids or modified or unmodified guar gums and celluloses, such as hydroxypropylated guar gum, methylhydroxyethylcellulose and hydroxypropylmethylcellulose.

Of course, one skilled in this art will take care to select the abovementioned optional additional compound or compounds and/or their amounts such that the advantageous properties, in particular the synergistic effect, intrinsically associated with the combination in accordance with the invention are not, or not substantially, detrimentally affected by the envisaged addition or additions.

The compositions according to the invention can be formulated according to techniques well known to this art, in particular those suited for the preparation of emulsions of oil-in-water or water-in-oil type.

These compositions can be provided, in particular, in the form of a simple or complex emulsion (O/W, W/O, O/W/O or W/O/W), such as a cream or a milk, or in the form of a gel or of a cream gel, or in the form of a lotion, of a powder or of a solid tube and can optionally be packaged as an aerosol and provided in the form of a foam or spray.

The compositions according to the invention are preferably formulated an oil-in-water or water-in-oil emulsion.

When an emulsion, the aqueous phase thereof can comprise a nonionic vesicular dispersion, prepared according to known processes (Bangham, Standish and Watkins, *J. Mol. Biol.*, 13, 238 (1965), FR-2,315,991 and FR-2,416,008).

The cosmetic compositions of the invention are useful in a regime or regimen for protecting the human epidermis or the hair against ultraviolet irradiation, as an antisun/ sunscreen composition or as a makeup product.

When the cosmetic compositions according to the invention are used for the protection of the human epidermis against UV rays or as an antisun/sunless composition, they can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid tube, powder, stick, aerosol foam or spray.

When the cosmetic compositions according to the invention are used for the protection of the hair against UV rays, they can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow-drying or hair setting, or a composition for perming or straightening, dyeing or bleaching the hair.

When the compositions are used as a product for making up the eyelashes, eyebrows or skin, such as a treatment cream for the epidermis, foundation, lipstick, eyeshadow, face powder, mascara or eyeliner, it can be provided in the anhydrous or aqueous, pasty or solid form, such as oil-in-water or water-in-oil emulsions, nonionic vesicular dispersions, or suspensions.

For purposes of illustration, for the antisun/sunscreen formulations in accordance with the invention which contain a vehicle of oil-in-water emulsion type, the aqueous phase (comprising in particular the hydrophilic UV-screening agents) generally constitutes from 50% to 95% by weight, preferably from 70% to 90% by weight, with respect to the entire formulation, the oily phase (comprising in particular the lipophilic UV-screening agents) from 5% to 50% by weight, preferably from 10% to 30% by weight, with respect to the entire formulation, and the (co)emulsifier(s) from 0.5% to 20% by weight, preferably from 2% to 10% by weight, with respect to the total weight of the formulation.

In order to further illustrate the present invention and the advantages thereof, the following specific examples are given, it being understood that same are intended only as illustrative and in nowise limitative.

EXAMPLE 1

The following specific composition according to the present invention was formulated via simple intimate admixing of the several constituents thereof:

80/20 Mixture of cetearyl alcohol and of

| | |
|---|---|
| oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| $C_{12}$–$C_{15}$ Alkyl benzoate (Witconol TN, Witco) | 20 g |
| n-Hexyl 2-(4-diethylamino-2-hydroxybenzoyl)benzoic | 2 g |
| Glycerol | 10 g |
| Butyl Methoxydibenzoylmethane (Parsol 1789, Hoffmann-LaRoche) | 2 g |

-continued

| | |
|---|---|
| Drometrizole Trisiloxane (Silatrizole, Rhodia Chimie) | 2 g |
| Preservatives | q.s. |
| Demineralized water | q.s. for 100 g |

EXAMPLE 2

The following specific composition according to the present invention was formulated via simple intimate admixing of the several constituents thereof:

| | |
|---|---|
| Glycerol mono/distearate/polyethylene glycol (100 EO) stearate mixture (Arlacel 165 FL, ICI) | 2 g |
| Stearyl alcohol (Lanette 18, Henkel) | 1 g |
| Palm oil stearic acid (Stéarine TP, Stéarinerie Dubois) | 2.5 g |
| Polydimethylsiloxane (Dow Corning 200 Fluid, Dow Corning) | 0.5 g |
| $C_{12}/C_{15}$ Alkyl benzoate (Witconol TN, Witco) | 18 g |
| Triethanolamine | 0.5 g |
| n-Hexyl 2-(4-diethylamino-2-hydroxybenzoyl)benzoic | 2.5 g |
| Drometrizole Trisiloxane (Silatrizole, Rhodia Chimie) | 2 g |
| Butyl Methoxydibenzoylmethane (Parsol 1789, Hoffmann-LaRoche) | 1.5 g |
| Glycerol | 5 g |
| Hexadecyl phosphate, potassium salt (Amphisol K, Hoffmann-LaRoche) | 1 g |
| Polyacrylic acid (Synthalen K, 3 V) | 0.3 g |
| Hydroxypropyl methyl cellulose (Methocel F4M, Dow Chemical) | 0.1 g |
| Triethanolamine | q.s. pH 7 |
| Preservatives | q.s. |
| Demineralized water | q.s. for 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological sunscreen composition suited for the UV-photoprotection of human skin and/or hair, comprising synergistically UV-$A_{PPD}$-enhancing amounts of (i) at least one UV-screening silicon compound having a benzotriazole functional group substituent, (ii) at least one UV-screening dibenzoylmethane compound, and (iii) at least one UV-screening amino-substituted 2-hydroxybenzophenone compound having the following structural formula (III):

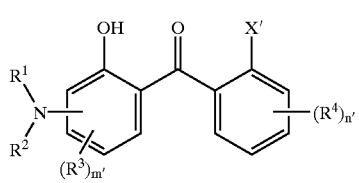

(III)

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a ($C_1$–$C_{20}$)alkoxycarbonyl radical, a $C_1$–$C_{12}$ alkylamino radical, a di($C_1$–$C_{12}$)alkylamino radical, an aryl radical or a heteroaryl radical which is optionally substituted, or a water-solubilizing substituent selected from among a carboxylate group, a sulfonate group or an ammonium residue; X' is a hydrogen atom or a —COOR$^5$ or —CONR$^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(Y'O)$_o$—Z' radical or an aryl radical; Y' is —(CH$_2$)$_2$—, —(CH$_2$)$_3$—, —(CH$_2$)$_4$— or —CH—(CH$_3$)—CH$_2$—; Z' is —CH$_2$—CH$_3$, —CH$_2$CH$_2$CH$_3$, —CH$_2$—CH$_2$—CH$_2$—CH$_3$ or —CH(CH$_3$)—CH$_3$; m' is an integer ranging from 0 to 3; n' is an integer ranging from 0 to 3; and o is an integer ranging from 1 to 2, formulated into (iv) a topically applicable, cosmetically/dermatologically acceptable vehicle, diluent or carrier therefor.

2. The cosmetic/dermatological sunscreen composition as defined by claim 1, said first, second and third UV-screening compounds being present therein in a proportion eliciting a synergistic effect with regard to the sun protection factors UV-$A_{PPD}$ conferred.

3. The cosmetic/dermatological sunscreen composition as defined by claim 1, said silicon compound having a benzotriazole functional group substituent comprising a silane and/or polyorganosiloxane with a benzotriazole functional group and including at least one structural unit of the following formula (1):

$$O_{(3-a)/2}Si(R_7)_a—G \quad (1)$$

in which $R_7$ is an optionally halogenated $C_1$–$C_{10}$ alkyl radical, or a phenyl radical, or a trimethylsilyloxy radical, a is an integer ranging from 0 to 3, inclusive; and G is a monovalent radical bonded directly to a silicon atom and which corresponds to the following structural formula (2):

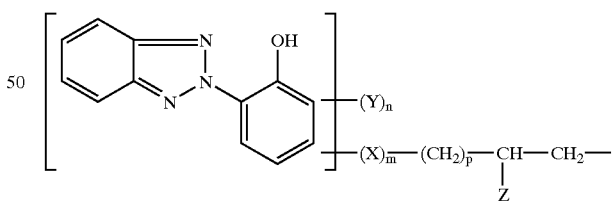

(2)

in which the radicals Y, which may be identical or different, are each a $C_1$–$C_8$ alkyl radical, a halogen or a $C_1$–$C_4$ alkoxy radical, with the proviso that, in the latter event, two adjacent Y radicals on the same aromatic nucleus can together form an alkylidenedioxy group in which the alkylidene group contains from 1 to 2 carbon atoms; X is O or NH; Z is hydrogen or a $C_1$–$C_4$ alkyl radical; n is an integer ranging from 0 to 3, inclusive; m is 0 or 1, and p is an integer ranging from 1 to 10, inclusive.

4. The cosmetic/dermatological sunscreen composition as defined by claim 3, said silicon compound having a benzotriazole functional group substituent corresponding to one of the following formulae (5) or (6):

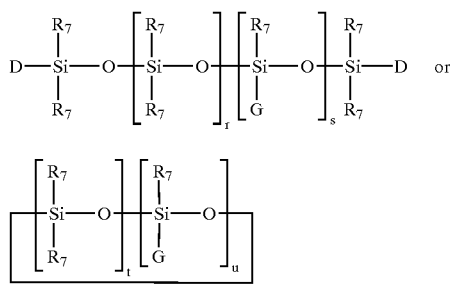

in which the radicals $R_7$, which may be identical or different, are each a $C_1$–$C_{10}$ alkyl, phenyl, 3,3,3-trifluoropropyl or trimethylsilyloxy radical, at least 80% by number of the $R_7$ radicals being methyl; the radicals D, which may be identical or different, are each an $R_7$ radical or the G radical; r is an integer ranging from 0 to 50, inclusive, and s is an integer ranging from 0 to 20 inclusive, and, if s=0, at least one of the two D radicals is a radical G; u is an integer ranging from 1 to 6, inclusive, and t is an integer ranging from 0 to 10, inclusive, with the proviso that t+u is equal to or greater than 3.

5. The cosmetic/dermatological sunscreen composition as defined by claim 4, said silicon compound having a benzotriazole functional group substituent corresponding to the following formula (7):

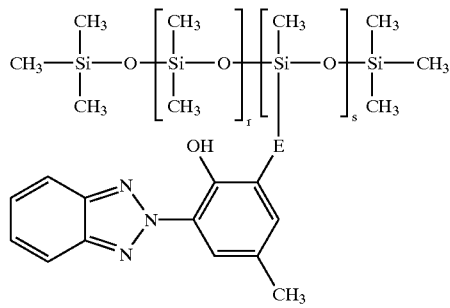

with $0 \leq r \leq 10$, $1 \leq s \leq 10$, and where E represents the divalent radical:

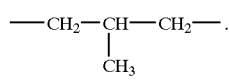

6. The cosmetic/dermatological sunscreen composition as defined by claim 5, said silicon compound having a benzotriazole functional group substituent comprising Drometrizole Trisiloxane of the following formula:

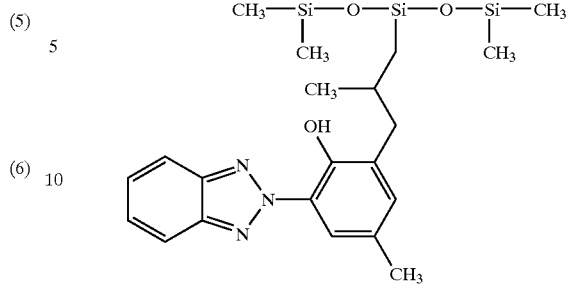

7. The cosmetic/dermatological sunscreen composition as defined by claim 1, said silicon compound having a benzotriazole functional group substituent comprising from 0.5% to 15%, by weight, with respect to the total weight thereof.

8. The cosmetic/dermatological sunscreen composition as defined by claim 1, said at least one UV-screening dibenzoylmethane compound comprising 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and/or 2,6-dimethyl-4-tert-butyl-4'-methoxydibenzoylmethane.

9. The cosmetic/dermatological sunscreen composition as defined by claim 8, said at least one UV-screening dibenzoylmethane compound comprising 4-tert-butyl-4'-methoxydibenzoylmethane.

10. The cosmetic/dermatological sunscreen composition as defined by claim 8, said at least one UV-screening dibenzoylmethane compound comprising 4-isopropyldibenzoylmethane.

11. The cosmetic/dermatological sunscreen composition as defined by claim 1, said at least one UV-screening dibenzoylmethane compound comprising from 0.5 to 15% by weight, with respect to the total weight thereof.

12. The cosmetic/dermatological sunscreen composition as defined by claim 1, said at least one UV-screening amino-substituted 2-hydroxybenzophenone compound of formula (III) having the following structural formula (IIIa):

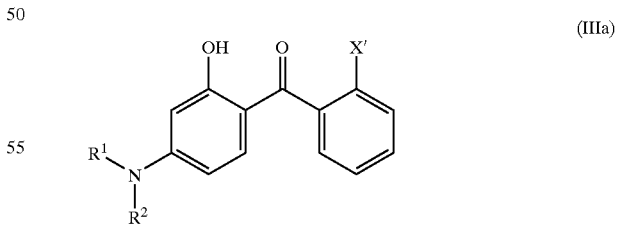

in which $R^1$ and $R^2$, which may be identical or different, are each a hydrogen atom, or a $C_1$–$C_{12}$ alkyl radical, or together form, with the nitrogen atom to which they are bonded, a 5- or 6-membered heterocyclic ring member; X' is —$COOR^5$ or —$CONR^6R^7$; $R^5$ is a hydrogen atom, a $C1$–$C_{12}$ alkyl radical or a $C_3$–$C_6$ cycloalkyl radical; and $R^6$ and $R^7$, which may be identical or different, are each a hydrogen atom, a $C_1$–$C_{12}$ alkyl radical or a $C_5$–$C_6$ cycloalkyl radical.

13. The cosmetic/dermatological sunscreen composition as defined by claim 12, wherein formula (IIIa), $R^1$ and $R^2$, which may be identical or different, are each a $C_1$–$C_4$ alkyl radical; $R^5$ is a $C_3$–$C_8$ alkyl radical; and $R^6$ and $R^7$, which may be identical or different, are each a $C_1$–$C_8$ alkyl radical.

14. The cosmetic/dermatological sunscreen composition as defined by claim 1, said at least one UV-screening Composition amino-substituted 2-hydroxybenzophenone compound of formula (III) having the following structural formula (IIIb):

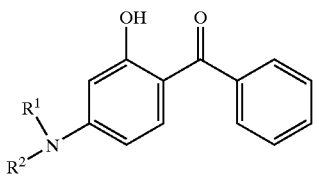

(IIIb)

in which $R^1$ and $R^2$, which may be identical or different, are each a $C_1$–$C_{12}$ alkyl radical, or together form, with the nitrogen atom to which they are bonded, a 5-or 6-membered heterocyclic ring member.

15. The cosmetic/dermatological sunscreen composition as defined by claim 14, said at least one compound of formula (IIIb) comprising 4-diethylamino-2-hydroxyphenyl phenyl ketone and/or 4-pyrrolidino-2-hydroxyphenyl phenyl ketone.

16. The cosmetic/dermatological sunscreen composition as defined by claim 1, said at least one UV-screening amino-substituted 2-hydroxybenzophenone compound of formula (III) having the following structural formula (IIIc):

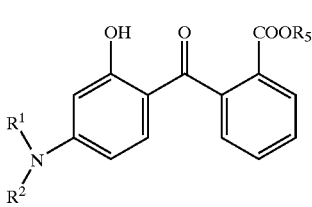

(IIIc)

in which $R^1$ and $R^2$, which may be identical or different, are each a hydrogen atom, or a $C_1$–$C_8$ alkyl radical, or together form, with the nitrogen atom to which they are bonded, a 5- or 6-membered heterocyclic ring member; and $R^1$ is a hydrogen atom, a $C_1$–$C_{12}$ alkyl radical or a $C_3$–$C_6$ cycloalkyl radical.

17. The cosmetic/dermatological sunscreen composition as defined by claim 16, said at least one compound of formula (IIIc) comprising 2-(4-pyrrolidino-2-hydroxybenzoyl)benzoic acid, methyl 2-(4-diethylamino-2-hydroxybenzoyl)benzoate, 2-ethylhexyl 2-(4-diethylamino-2-hydroxybenzoyl)-benzoate, cyclohexyl 2-(4-diethylamino-2-hydroxybenzoyl)-benzoate, n-hexyl 2-(4-diethylamino-2-hydroxybenzoyl)benzoate, 2-(4-dibutylamino-2-hydroxybenzoyl)benzoic acid, methyl 2-(4-dibutylamino-2-hydroxybenzoyl)benzoate and/or isobutyl 2-(4-dibutylamino-2-hydroxybenzoyl)benzoate.

18. The cosmetic/dermatological sunscreen composition as defined by claim 17, said at least one compound of formula (IIIc) comprising n-hexyl 2-(4-diethyl-amino-2-hydroxybenzoyl)benzoate.

19. The cosmetic/dermatological sunscreen composition as defined by claim 1, said at least one UV-screening amino-substituted 2-hydroxybenzophenone compound of formula (III) comprising from 0.1% to 20% by weight, with respect to the total weight thereof.

20. The cosmetic/dermatological sunscreen composition as defined by claim 19, said at least one UV-screening amino-substituted 2-hydroxybenzophenone compound of formula (III) comprising from 0.1% to 20% by weight, with respect to the total weight thereof.

21. The cosmetic/dermatological sunscreen composition as defined by claim 20, said at least one UV-screening amino-substituted 2-hydroxybenzophenone compound of formula (III) comprising from 0.5% to 10% by weight, with respect to the total weight thereof.

22. The cosmetic/dermatological sunscreen composition as defined by claim 1, additionally comprising at least one other organic screening agent which is active in the UV-A and/or UV-B regions.

23. The cosmetic/dermatological sunscreen composition as defined by claim 22, said additional organic UV screening agent or agents being selected from among anthranilates; cinnamic derivatives; salicylic derivatives; camphor derivatives; triazine derivatives; benzophenone derivatives, other than those of formula (III); β,β-diphenylacrylate derivatives; benzotriazole derivatives; benzalmalonate derivatives; benzimidazole derivatives; imidazolines; bisbenzoazolyl derivatives; p-aminobenzoic acid (PABA) derivatives; methylenebis(hydroxyphenylbenzotriazole) derivatives; screening polymers and screening silicones, other than benzotriazole silicon compounds; dimers derived from α-alkylstyrene; and 4,4-diarylbutadienes.

24. The cosmetic/dermatological sunscreen composition as defined by claim 23, said organic UV screening agent or agents being selected from among Ethylhexyl Salicylate, Octocrylene, Ethylhexyl Methoxycinnamate, Butyl Methoxydibenzoylmethane, Phenylbenzimidazole Sulfonic Acid, Benzophenone-3, Benzophenone-4, Benzophenone-5, 4-Methylbenzylidene camphor, Disodium Phenyl Dibenzimidazole Tetrasulfonate, Anisotriazine, Ethylhexyl triazone, Diethylhexyl Butamido Triazone, 2,4,6-Tris(diisobutyl 4'-aminobenzalmalonate)-s-triazine, Methylenebis(benzotriazolyltetramethylbutyl-phenol), 1,1-disodium (2,2'dimethylpropyl)-4,4'-diphenylbutadiene, and mixtures thereof.

25. The cosmetic/dermatological sunscreen composition as defined by claim 1, additionally comprising coated or uncoated metal oxide pigments or nanopigments.

26. The cosmetic/dermatological sunscreen composition as defined by claim 25, said pigments or nanopigments comprising coated or uncoated titanium dioxide, zinc oxide, iron oxide, zirconium oxide or cerium oxide, and mixtures thereof.

27. The cosmetic/dermatological sunscreen composition as defined by claim 1, additionally comprising at least one agent for the artificial tanning and/or browning of the skin.

28. The cosmetic/dermatological sunscreen composition as defined by claim 1, additionally comprising at least one adjuvant or additive selected from among fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, or colorants.

29. The cosmetic/dermatological sunscreen composition as defined by claim 1, formulated as a nonionic vesicular dispersion, an O/W or W/O emulsion, a cream, a milk, a gel, a cream gel, a suspension, a dispersion, a powder, a solid tube, a foam or a spray.

30. The cosmetic/dermatological sunscreen composition as defined by claim 1, formulated as a makeup for the eyelashes, eyebrows or skin and provided in the anhydrous or aqueous, pasty or solid form, in the form of an emulsion, of a suspension or of a dispersion.

31. The cosmetic/dermatological sunscreen composition as defined by claim 1, formulated for the protection of the hair against ultraviolet rays and provided in the form of a shampoo, of a lotion, of a gel, of an emulsion, or of a nonionic vesicular dispersion.

32. A regime or regimen for photoprotecting human skin, and/or hair against the deleterious effect of ultraviolet irradiation, comprising topically applying thereon an effective amount of a cosmetic/dermatological sunscreen composition which comprises synergistically UV-$A_{PPD}$-enhancing amounts of (i) at least one UV-screening silicon compound having a benzotriazole functional group substituent, (ii) at least one UV-screening dibenzoylmethane compound, and (iii) at least one UV-screening amino-substituted 2-hydroxybenzophenone compound having the following structural formula (III):

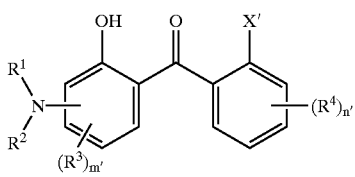

(III)

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a ($C_1$–$C_{20}$)alkoxycarbonyl radical, a $C_1$–$C_{12}$ alkylamino radical, a di($C_1$–$C_{12}$)alkylamino radical, an aryl radical or a heteroaryl radical which is optionally substituted, or a water-solubilizing substituent selected from among a carboxylate group, a sulfonate group or an ammonium residue; X' is a hydrogen atom or a —$COOR^5$ or —$CONR^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —$(Y'O)_o$—$Z'$ radical or an aryl radical; Y' is —$(CH_2)_2$—, —$(CH_2)_3$—, —$(CH_2)_4$— or —CH—$(CH_3)$—$CH_2$—; Z' is —$CH_2$—$CH_3$, —$CH_2CH_2CH_3$, —$CH_2$—$CH_2$—$CH_2$—$CH_3$ or —CH$(CH_3)$—$CH_3$; m' is an integer ranging from 0 to 3; n' is an integer ranging from 0 to 3; and o is an integer ranging from 1 to 2, formulated into (iv) a topically applicable, cosmetically/dermatologically acceptable vehicle, diluent or carrier therefor.

* * * * *